United States Patent
Eigenthaler et al.

(10) Patent No.: US 6,649,421 B1
(45) Date of Patent: Nov. 18, 2003

(54) ANTIBODIES AGAINST PHOSHORYLATED VASP (VASODILATOR-STIMULATED PHOSPHOPROTEIN), HYBRIDOMA CELLS FOR THEIR PREPARATION, AND THEIR USE

(75) Inventors: Martin Eigenthaler, Würzburg (DE); Heinz Hoschuetzky, Denzlingen (DE); Ulrich Walter, Veitshöchheim (DE)

(73) Assignee: Vasopharm Biotech GmbH, Wuerzburg (DE)

( * ) Notice: Subject to any disclaimer, the term of this patent is extended or adjusted under 35 U.S.C. 154(b) by 0 days.

(21) Appl. No.: 09/530,864

(22) PCT Filed: Nov. 6, 1998

(86) PCT No.: PCT/EP98/07103

§ 371 (c)(1),
(2), (4) Date: Jun. 21, 2000

(87) PCT Pub. No.: WO99/24473

PCT Pub. Date: May 20, 1999

Related U.S. Application Data

(60) Provisional application No. 60/079,375, filed on Mar. 26, 1998.

(30) Foreign Application Priority Data

Nov. 7, 1997 (DE) .......................... 197 49 091

(51) Int. Cl.$^7$ ............................................. G01N 33/543
(52) U.S. Cl. ................... 436/548; 435/70.2; 435/70.21; 436/512; 436/513; 436/547; 530/388.1; 530/388.15; 530/866
(58) Field of Search ............................ 435/70.2, 70.21; 436/512, 513, 547, 548; 530/388.1, 388.15, 866

(56) References Cited

U.S. PATENT DOCUMENTS 5,599,681 A    2/1997   Epstein et al. ............. 435/7.23

FOREIGN PATENT DOCUMENTS

WO    WO 93/21230    10/1993

OTHER PUBLICATIONS

Abel, et al., "Monoclonal antibodies against the focal adhesion protein VASP revealing epitopes involved in the interaction with two VASP binding proteins and VASP phosphorylation," European Journal of Cell Biology, vol. 69, No. Suppl. 42, p. 39; 21$^{st}$ Meeting of the German Society for Cell Biology, Hamburg, Germany, Mar. 24–28 (1996).

Butt, et al., "cAMP–and cGMP–dependent protein kinase phosphorylation sites of the focal adhesion vasodilator-stimulated phosphoprotein (VASP) in vitro and in intact human platelets," J. Biol. Chem., vol. 269, No. 20, pp. 14509–14517 (1994).

Eigenthaler, M., et al., "Concentration and regulation of cyclic nucleotides, cyclic–nucleotide–dependent protein kinases and one of their major substrates in human platelets," Eur. J. Biochem., vol. 205, pp. 471–481 (1992).

Haffner, et al., "Molecular cloning, structural analysis and functional expression of the proline–rich focal adhesion and microfilament–associated protein VASP," EMBO J., vol. 14, No. 1, pp. 19–27 (1995).

Halbrügge, M., et al., "Stoichiometric and reversible phosphorylation of a 46–kDa protein in human platelets in response to cGMP– and cAMP–elevating vasodilators." J. Biol. Chem., vol. 265, pp. 3088–3093 (1990).

Horstrup, et al., "Phosphorylation of focal adhesion vasodilator–stimulated phosphoprotein at Ser157 in intact human platelets correlates with fibrinogen receptor inhibition," Eur. J. Biochem., vol. 225, pp. 21–27 (1994).

Jarchau, T., et al., "Purification and assays of vasodilator-stimulate phosphoprotein," Methods in Enzymology, vol. 298, pp. 103–113 (1998).

Reinhard, M., et al., "The 46/50 kDa phosphoprotein VASP purified from human platelets is a novel protein associated with actin filaments and focal contacts," EMBO Journal, vol. 11, No. 6, pp. 2063–2070 (1992).

Smolenski, Albert, et al., "Analysis and regulation of vasodilator–stimulated phosphoprotein serine 239 phosphorylation in vitro and in intact cells using a phosphospecific monoclonal antibody," J. Biol. Chem., vol. 273, No. 32, pp. 20029–20035 (1998).

Walter, U., "Biochemical parameters of Endothelial Function," Institute for Clinical Biochemistry and Pathobiochemistry, Blick, Würzburg University, pp. 79–81 (1997) (German with English translation).

Walter, U., et al., "Platelet–Vessel wall interactions, focal adhesions, and the mechanism of action of endothelial factors," AAS 45, Mediators in the Cardiovascular System: Regional Ischemia, pp. 255–268 (1995).

*Primary Examiner*—Bao-Thuy L. Nguyen
(74) *Attorney, Agent, or Firm*—Finnegan, Henderson, Farabow, Garrett, & Dunner, L.L.P.

(57) ABSTRACT

The invention relates to antibodies against VASP (vasodilator-stimulated phosphoprotein) which only bind VASP as an antigen when VASP is present in phosphorylated form, to hybridoma cells for their preparation, and to the use of the antibodies or antibody fragments as diagnostic agents and/or therapeutic agents.

3 Claims, No Drawings

ANTIBODIES AGAINST PHOSHORYLATED VASP (VASODILATOR-STIMULATED PHOSPHOPROTEIN), HYBRIDOMA CELLS FOR THEIR PREPARATION, AND THEIR USE

This application claims the benefit of provisional application No. 60/079,375, filed Mar. 26, 1998, the content of which is incorporated herein by reference.

The invention relates to antibodies against VASP (vasodilator-stimulated phosphoprotein) which only bind VASP as antigen when VASP is present in phosphorylated form, to hybridoma cells for their preparation, and to the use of the antibodies or antibody fragments as diagnostic agents and/or therapeutic agents.

Diseases of the vascular system are responsible for a large number of chronic and life-threatening diseases, such as cardiac infarction, stroke, arterial occlusion disease and many forms of kidney failure.

The endothelial cells, which, inter alia, control the blood coagulation system, the functional state of the thrombocytes, the migration of inflammatory and tumor cells into the vascular wall, the state of contraction and growth of smooth muscle cells and consequently also blood pressure and vascular wall structure and also neovascularization, are of particular importance for regulating the vascular system. Many of these vascular wall functions are disturbed in serious vascular diseases, a situation which can in the end lead to cardiac infarction, stroke and many forms of kidney failure.

The endothelium forms the important substances prostacyclin ($PGI_2$) and nitrogen monoxide (NO), which is also known as endothelium-derived relaxing factor (EDRF), which substances inhibit both the thrombocytes and the vascular muscle cells. The endothelial functions are controlled by said endothelial factors such as prostacyclin ($PGI_2$) or EDRF, e.g. NO.

Consequently, in order to treat diseases which are associated with an endothelial dysfunction in a specific manner, it is necessary to develop biochemical parameters which enable an endothelial dysfunction to be diagnosed and its course to be controlled.

It is desirable to be able to recognize endothelial dysfunctions as early as possible, that is at a stage at which irreversible damage, such as atherosclerotic lesions, caused by endothelial dysfunctions has still not manifested itself.

Identification of an endothelial dysfunction at an early stage makes it possible to develop new therapeutic approaches which can bring about reversible treatment of the endothelial dysfunction.

Methods which are known for determining in-vivo endothelial functions are invasive detection methods, such as quantitative angiography, or else non-invasive, image-providing methods. Disadvantages of these methods are that these investigations are carried out directly on the patient, and are difficult to quantify and very expensive.

It is therefore also desirable to have available biochemical/immuno-biological methods which make it possible to determine endothelial functions rapidly and simply in biological material ex vivo, for example in cell samples or blood samples by means of routine investigations in the laboratory. Endothelial functions are those functions which can be regulated by endothelial factors such as prostacyclin ($PGI_2$) or EDRF, e.g. NO.

It is an object of the invention to provide reagents for the evaluation and modulation of endothelial function. According to this and other objects of the invention, an antibody is provided which is directed to VASP (Vasodilator-stimulated phosphoprotein) and binds VASP only when VASP is phosphorylated.

In one aspect of the invention an antibody is disclosed which binds VASP only when VASP is phosphorylated at position serine 239 (phosphoserine 239 VASP). In another aspect an antibody is provided which binds VASP only when VASP is phosphorylated at position serine 157 (phosphoserine 157 VASP).

Different embodiments of the invention include polyclonal antibodies, monoclonal antibodies and antibody fragments. Other embodiments include a monoclonal antibody produced by the hybridoma cell line 16C2, and particularly Mab 16C2.

It is a further object of the invention to provide hybridoma cells which are useful in manufacturing the antibodies of the invention. Further to this object of the invention hybridoma cell line is provided which produces a monoclonal antibody against VASP which binds VASP only when it is phosphorylated. In one embodiment, the hybridoma cell line 16C2 (DSM ACC2330) is provided. p It is yet another object of the invention to provide methods of evaluating endothelial function. According to this object of the invention methods are provided for determining the phosphorylation status of VASP. In one aspect of the invention biological material is contacted with an antibody against VASP (vasodilator-stimulated phosphoprotein), which binds VASP as antigen only when VASP is phosphorylated.

In another aspect of the invention a quantitative method is provided which further involves quantifying the amount of VASP antibody which binds the biological material. A specific embodiment includes a Western blotting method, which entails resolving VASP by eletrophoresis and contacting, the VASP with an antibody against VASP, which binds VASP only when it is phosphorylated. Another embodiment is a flow cytometry method, which involves contacting a sample with an antibody against VASP which binds VASP only when it is phosphorylated.

In yet another aspect of the invention, methods of diagnosis are provided. A representative method entails contacting a sample with an antibody against VASP which binds VASP only when it is phosphorylated and evaluating the phosphorylation state of VASP. In one embodiment, this method involves quantitatively determining the phosphorylation of VASP in the sample. In another embodiment, methods are described where the antibody binds phosphoserine 239 VASP or phosphoserine 157 VASP. In still another embodiment, the sample is human thrombocytes or human whole blood.

It is yet another object of the invention to provide methods for detecting markers of endothelial function. In one aspect, a method for detecting substances which affect the level of cGMP and/or cAMP is provided which involves testing a sample from patient who has been exposed to a substance of affecting cGMP and/or cAMP levels, contacting the sample with an antibody against VASP which binds VASP only when it is phosphorylated and evaluating the phosphorylation state of VASP relative to a control sample.

In yet one more aspect, a method is detailed for detecting endothelial dysfunction which involves contacting a sample from a patient with an antibody against VASP which binds VASP only when it is phosphorylated and evaluating the phosphorylation state of VASP relative to a normal control sample.

It is a further object of the invention to provide a convenient kit for accomplishing the diagnostic methods disclosed herein. Further to this object a diagnostic kit is provided which contains an antibody against VASP which binds VASP only when it is phosphorylated.

It is still another object of the invention to provide methods of treating patients suffering from endothetial dysfunction. According to this and other a therapeutic objects of the invention a method of treatment is disclosed where a patient in need of treatment is administered a therapeutically effective amount of an antibody against VASP which binds VASP only when it is phophorylated.

Human VASP (vasodilator-stimulated phosphoprotein), which is phosphorylated in thrombocytes andvascular wall cells in response to hypotensive (vasodilatory) hormones and drugs, has recently been discovered, isolated and characterized from the point of view of molecular genetics (Haffner et al., EMBO J. 14, 19–27, 1995).

VASP is an important component of the ANF/NO/cGMP/cGMP protein kinase signal pathway, which is very important physiologically, pathophysiologically and pharmacologically, and also of the cAMP/cAMP protein kinase signal pathway (U. Walter, Blick 1/97 Würzburg University, pp. 79–81,1997). VASP is expressed in almost all human and animal cells, with particularly high concentrations being found in thrombocytes, vascular smooth muscle cells and fibroblasts. In cultured cells, VASP is associated with focal contacts (cell/matrix contact sites), cell/cell contacts, microfilaments and dynamic membrane regions (e.g. leading edge) (Walter et al., Agents and Actions 45S, 255–268, 1995).

The phosphorylation of VASP in the vascular system correlates with the inhibition of thrombocyte adhesion/aggregation, the inhibition of smooth muscle contraction/migration and the inhibition of paracellular endothelial permeability.

VASP is phosphorylated and dephosphorylated at three different sites (serine 157, serine 239 and threonine 278, see Horstrup et al., Eur. J. Biochem. 225, 21–27 (1994)). Serine 239 is occasionally also designated Serine 238, specifically when the first methionine of VASP is not included in the count.

VASP serine 239 is phosphorylated in intact human vascular cells (thrombocytes, endothelial cells and smooth muscle cells) in response to physiological and pharmacological NO donors and thrombocyte inhibitors and vasodilators.

The phosphorylation of VASP serine 239 is mediated, in particular, by cGMP-dependent protein kinases which are activated, by way of the cGMP, by important hormones such as natriuretic peptides or NO-releasing substances and drugs. Phosphorylation of VASP serine 239 is additionally mediated by cAMP-dependent protein kinases which are activated by way of cAMP-increasing hormones and drugs.

While cAMP-dependent protein kinases principally phosphorylate the serine 157 position, they also phosphorylate the serine 239 position of the VASP. VASP phosphorylation at the serine 157 position has also been observed to be closely correlated with inhibition of the binding of fibrinogen to glycoprotein IIb-IIIa in human blood platelets (Horstrup et al., Eur. J. Biochem. 225, 21–27 (1994))

Determination of the degree to which VASP was phosphorylated in biological material, for example in extracts of tissues and cells, in particular determination of the phosphorylation of VASP at position 239 and/or position 157, would be an important biochemical parameter whose measurement would make it possible to develop a diagnostic system for detecting all cGMP-increasing and/or cAMP-increasing hormones or drugs, such as atrial natriuretic factor (ANF), guanylin, NO-releasing substances and drugs, and furthermore enable conclusions to be drawn with regard to in-vivo endothelial functions.

Antibodies that specifically bind to reversibly phosphorylated proteins have been described in U.S. Pat. No. 5,599,681, WO93/21230 and U. Walter, Blick 1/97 Wüjrzburg University, pp. 79–81,1997.

The object of the present invention was to develop biochemical/immuno-biological methods which enable the phosphorylation status of VASP in biological material to be determined qualitatively and/or quantitatively in a rapid in simple manner.

This object was achieved by the provision of antibodies which only bind VASP as antigen when the VASP is present in phosphorylated form.

The invention consequently relates, in a quite general manner, to antibodies which only bind VASP as antigen when VASP is present in phosphorylated form.

Within the meaning of the invention, antibodies are to be understood as being both polyclonal antibodies and monoclonal antibodies (Mabs) and a their fragments, and also SCF fragments or other synthetic or recombinant protein domains, which specifically recognize phosphorylated regions in the VASP.

Fragments of antibodies include any portion of the antibody which is capable of binding the target antigen, in this case VASP or a specific portion thereof. Antibody fragments specifically include F(ab')$_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, Coligan et al., eds., (John Wiley & Sons 1991–92).

F(ab')$_2$ fragments are typically about 110 kDa (IgG) or about 15G kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IdM) and can be formed, for example, by reducing the disulfide bond(s) of an F(ab')$_2$ fragment. The resulting free sulfhydryl group(s) may be used to conveniently conjugate Fab' fragments to other molecules, such as detection reagents (e.g., enzymes). Fab fragments are monovalent and usually are about 50 kDa (from any source). Fab fragments include the light (L) and heavy (H) chain, variable ($V_L$ and $V_H$, respectively) and constant ($C_L C_H$, respectively) regions of the antigen-binding portion of the antibody. The H and L portions are linked by an intramolecular disulfide bridge.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interacts and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers. The resulting Fv is now a single chain (i.e., SCFv).

One preferred method involves the generation of SCFvs by recombinant methods, which allows the generation of Fvs with new specificities by mixing and matching variable chains from different antibody sources. In a typical method, a recombinant vector would be provided which comprises the appropriate regulatory elements driving expression of a cassette region. The cassette region would contain a DNA enclosing a peptide linker, with convenient sites at both the 5' and 3' ends of the linker for generating fusion proteins. The DNA encoding a variable region(s) of interest may be cloned in the vector from fusion proteins with the linker, thus generating an SCFv.

In an exemplary alternative approach, DNAs encoding two Fvs may be ligated to the DNA encoding the linker, and the resulting tripartite fusion may be ligated directly into a conventional expression vector. The SCFv DNAs generated any of these methods may be expressed in prokaryotic or eukaryotic cells, depending on the vector chosen.

Preference is given to monoclonal antibodies and their fragments which only bind VASP as antigen when VASP is present in phosphorylated form.

Particular preference is furthermore given to monoclonal antibodies and their fragments which only bind VASP, or peptides which encompass the peptide sequence around serine 239 of VASP, as antigen when the serine at position 239 is phosphorylated (phosphoserine 239 VASP).

Within the meaning of the invention, the term VASP is also to be understood as meaning derivatives of VASP, i.e. functionally equivalent moieties, mutants, fragments or variants of VASP, for example phospho-serine 239 VASP which is additionally phosphorylated at position serine 157 and/or threonine 278, and also, for example, glycosylation mutants and other covalent modifications and structural elements which are of importance for protein/protein interaction. Within the meaning of the invention, the term VASP encompasses both human VASP and VASP from other species, in particular from mammals such as rat, mouse, rabbit, dog, pig or monkey. Antibodies may be produced by conventional methods for instance according to the technique described by Köhler and Milstein (Köhler and Milstein, Nature 256; 495, 1975). Typically, where selectivity based on phosphorylation state is desired, antibodies are raised against the phosphorylated forms of VASP. The antibodies isolated may be screened using conventional methods to ascertain selectivity. Preferably, antibodies are raised against peptide fragments of VASP which contain serine 157, serine 239 and/or thereonine 278.

The length of the antigenic VASP peptide is unimportant, so long as it is capable of eliciting a humoral response. Typical antigenic peptides are less than about 50 amino acids long. Some preferred peptides are less than about 20 amino acids in length. Most preferred peptides are between about 6 and about 12 amino acids long. Preferred peptides include KLRKVS$^{239}$ KQ or RKVS$^{239}$ KQE. The peptide preferably is phosphorylated at serine 157, serine 239 and/or threonine 278. Peptides may be obtained by recombinant means. Typically, they are produced either by proteolytic degradation of VASP or in vitro synthesis and phosphorylation.

Preference is furthermore given to monoclonal antibodies which exhibit the abovementioned properties and which can be employed in flow cytometry, This requires the specificity of the novel antibodies to be retained even when the antigen is subjected to conditions which may alter the conformation of the antigen, as is to be expected in the fixation steps which are customarily employed in flow cytometry. The novel antibodies can, for example, be examined for their suitability for use in flow cytometry simply by means of testing them out.

The monoclonal antibody 16C2 is particularly preferred.

The novel antibodies may be prepared using methods which are known per se to the skilled person. The preparation of hybridoma cells using the technique described by Köhler and Milstein (Köhler and Milstein, Nature 256; 495, 1975) may, in particular, be mentioned for preparing monoclonal antibodies. The specificity of the purified antibodies can be checked, for example, using the following test methods:

a) Western blotting using recombinant VASP which is phosphorylated by cAMP-dependent or cGMP-dependent protein kinases to differing extents, in association with which it must only be possible to observe a positive signal with phosphorylated VASP.

b) Western blotting using extracts of cells, for example Pkt2 cells, which have been transfected with human VASP or with VASP which has been mutated in different ways and in which in each case one of the three phosphorylation sites has been mutated and thereby eliminated (S157A) VASP, (S239A) VASP and (T278A) VASP), and, in each case, human cGMP protein kinase. Those antibodies are suitable in which the positive signals in the Western blot are eliminated by the S239A mutation but not by the other two mutations.

c) Western blotting using human thrombocytes which have been treated with different vasodilators (e.g. prostacyclin or NO donors) or activators of cAMP protein kinase or cGMP protein kinase. The antibody is then suitable when a specific band is detected in the extract only with phosphorylated VASP. The antibodies can also be screened in an analogous manner using human fibroblasts and also rat and mouse thrombocytes.

d) Immunofluorescence investigations using fixed human thrombocytes and endothelial cells. A positive signal is observed when VASP is present as a phosphoprotein.

The invention furthermore relates to hybridoma cell lines which produce novel monoclonal antibodies, with the hybridoma cell line 16C2, which produces the monoclonal antibody 16C2, being particularly preferred.

The hybridoma cell line 16C2, which produces the monoclonal antibody 16C2, has been deposited in the Deutsche Sammiung von Mikroorganismen und Zelikulturen (German collection of microorganisms and cell cultures), Mascheroder Weg 1b, D-38124 Braunschweig, Germany, in accordance with the rules of the Budapest treaty on Nov. 6, 1997 under the following number: DSM ACC2330.

The novel antibodies are suitable for qualitatively and/or quantitatively, preferably quantitatively, determining both the phosphorylation of VASP which occurs under in-vitro conditions and that which occurs under in-vivo conditions, preferably for determining the serine 239 and/or serine 157 phosphorylation of VASP, particularly preferably for determining the serine 239 phosphorylation of VASP.

Quantitative methods of using antibodies are well known in the art and may be found, for example, in CURRENT PROTOCOLS IN IMMUNOLOGY, supra. These methods include enzyme-linked immunosorbant assays (ELISA) radioimmunoassays (RIAs) and the like.

The novel antibodies are furthermore suitable for qualitatively and/or quantitatively, preferably quantitatively, determining phosphorylated VASP, preferably phosphoserine 239 VASP and/or phosphoserine 157 VASP, particularly preferably phosphoserine 239 VASP, in biological material.

Biological material is, for example, understood as being: cell extracts, tissue extracts, cell slices, cell tissue and cells, such as thrombocytes, leukocytes, endothelial cells, smooth muscle cells and fibroblasts. The biological material can be derived from humans or else from other mammals such as rat, mouse, rabbit, dog, pig or monkey. Biological material of human origin is preferred.

The novel antibodies can be used to quantitatively determine phosphorylated VASP, in particular phosphoserine 157

VASP and/or phosphoserine 239 VASP, in biological material by means of quantitatively evaluating autoradiograms of Western blots in accordance with methods which are known to the skilled person, for example using NIH gel blotting Image 1.6 software, or else by means of immunofluorescence.

Due to the correlation which exists between the phosphorylation of serine 239 and serine 157 of VASP and the activity of cGMP-dependent and/or cAMP-dependent protein kinases, the novel antibodies are also suitable for use as agents for diagnosing cGMP signal pathways and cAMP signal pathways, in particular for diagnosing cGMP signal pathways.

The use of the novel antibodies to determine phosphoserine 239 VASP in biological material by means of the Western blotting technique and immunofluorescence also makes it possible to develop diagnostic methods for detecting cGMP-increasing substances, hormones or drugs. Examples which may be mentioned are: ANF, guanylin, NO-releasing substances or drugs. For example, control of the course and the therapy of NO donors can be monitored, which, inter alia, provides information on any nitrate tolerance phenomena which may develop.

Due to the correlation which exists between the phosphorylation of serine 157 of VASP and the activity of cAMP-dependent protein kinases, the novel antibodies can also be employed as agents for diagnosing cAMP-increasing substances, hormones or drugs.

The invention consequently also relates to the use of the novel antibodies or fragments thereof in diagnosis and/or therapy.

The novel diagnostic methods are methods which can be carried out in the laboratory, outside the human body (ex vivo).

The novel antibodies can be used for determining the degree of phosphorylation of VASP in biological material which derives from different species. Examples which may be mentioned are: man, rat, mouse, rabbit, dog, pig or monkey. Preference is given to using the novel antibodies for determining phosphorylated VASP in biological material from man, rat, mouse or dog. Particular preference is given to using the novel antibodies for determining phosphorylated VASP in human biological material.

The novel antibodies or fragments thereof can also be used in biosensors. Biosensors are known per se to the skilled person. Particular preference is given to a method which uses a second specific binding partner, such as an antibody, a lectin or a receptor. For detection and quantification in this case, one of the specific binding partners can carry a detectable label. These labels are known per se to the skilled person and can, for example, be a chromophore, a luminophore, a fluorophore, an enzyme, a radioactive isotope or a colored or colorless particle. Preference is given to a method in which the unlabeled, specific binding partner is coupled directly or indirectly, for example by way of another antibody or a biotinlavidin bridge, to a solid phase using methods known per se to the skilled person.

The novel antibodies or their fragments can also be radioactively labeled by methods known to the skilled person so that they can be used for immunoscintigraphy or else for immunotherapy. In addition, these monoclonal antibodies can be used as active compound carriers and employed for the therapy of diseases which are caused by endothelial dysfunctions.

Following analysis of the complete nucleotide sequence of the V genes of Mab 16C2, it is also technically possible to produce antibody constructs by, for example, inserting the hypervariable regions into a human Mab skeleton (Jones et al., Nature 321, 522–525, 1986; Verhoyen et al., Science 239,1534–1536,1988).

Preference is given to quantifying the antigen-bound antibody in blood platelets by means of flow cytometry, for example carried out on whole blood samples which have, where appropriate, been fixed using methods known to the skilled person. Methods for flow cytometry are known to the skilled person and can be carried out as described, for example, in G. Otten and W. M. Yokoyama (1992) Flow cytometry analysis using the Becton Dickinson FACScan, Current Protocols in Immunology, 5.4.1–5.4.19.

The flow-cytometric analysis of VASP phosphorylation, in particular VASP serine 239 phosphorylation, using the novel antibodies is not restricted to human thrombocytes and can also be carried out on other cell types such as lymphocytes, monocytes, leukocytes, endothelial cells and smooth muscle cells.

The use of flow cytometry to determine the phosphorylation of VASP, in particular of phosphoserine 239 VASP, in freshly withdrawn human thrombocytes with the aid of the novel antibodies makes it possible to determine ex vivo the in vivo activity of endothelial factors such as NO and prostacyclin and consequently to assess endothelial function or endothelial dysfunction in cardiovascular disorders as are found, for example, in arteriosclerosis, hypertension, diabetes, cardiac insufficiency and renal insufficiency.

Determining VASP phosphorylation, in particular VASP serine 239 phosphorylation, with the aid of the novel antibodies also makes it possible to control the therapy of the abovementioned diseases. The development of resistances to therapy, such as nitrate tolerance, can also be determined.

The novel antibodies can also be employed as therapeutic agents in that they affect the phosphorylation status of VASP, and/or its interactions with proteins, in biological material.

The invention consequently also relates to pharmaceutical preparations which comprise at least one of the novel antibodies.

The novel preparations may be used enterally (orally), parenterally (intravenously), rectally or locally (topically). They can be administered in the form of solutions, powders (tablets or capsules including microcapsules), liposome preparations, lipid complexes, colloidal dispersions, injection solutions or suppositories. The pharmaceutically customary liquid or solid fillers and extenders, solvents, emulsifiers, glidants, taste corrigents, dyes and/or buffering substances are suitable auxiliary substances for formulations of this nature. 0.1–100 mg are administered per kg of body weight as an expedient dose. They are expediently administered in dosage units which at least comprise the effective daily quantity of the novel antibodies, e.g. 30–3000 mg.

The daily dose which is to be administered depends on the body weight, age, sex and condition of the mammalian subject. However, higher or lower daily doses may also be called for. The daily dose can either be administered by being given on one occasion in the form of a single dosage unit or in the form of several smaller dosage units, or else being given on several occasions, at predetermined intervals, in the form of subdivided doses.

In order to produce pharmaceutical preparations, the novel antibodies can be worked into therapeutically inert organic and inorganic excipients. Lactose, corn starch or derivatives thereof, tallow and stearic acid or salts thereof are examples of such excipients for tablets, coated tablets and hard gelatin capsules. Water, polyols, sucrose, invert sugar and glucose are suitable excipients for preparing solutions. Water, alcohols, polyols, glycerol and vegetable oils are suitable excipients for injection solutions. Vegetable oils and hardened oils, waxes, fats and semisolid polyols are suitable excipients for suppositories. The pharmaceutical preparations can also comprise preservatives, solvents, stabilizers, wetting agents, emulsifiers, sweeteners, dyes, flavorings, salts for altering the osmotic pressure, buffers, coating agents, antioxidants and, where appropriate, other therapeutic active compounds.

The invention also relates to a process for preparing a novel pharmaceutical, wherein at least one of the novel antibodies is brought into a suitable administration form together with a pharmaceutically suitable and physiologically tolerated excipient and, where appropriate, other suitable active compounds, additives or auxiliary substances.

The invention furthermore relates, quite generally, to a diagnostic process for determining the phosphorylation of VASP, preferably the serine 239 phosphorylation of VASP, with the aid of other specific probes such as polygonal antibodies, SCFV fragments or other synthetic or recombinant protein domains which specifically recognize phosphorylated sequences in VASP, in particular in phosphoserine 239 VASP.

The invention furthermore also relates to a diagnostic process for determining the serine 157 phosphorylation and/or threonine 278 phosphorylation of VASP With the aid of specific probes such as monoclonal antibodies, polyclonal antibodies, SCFV fragments or other synthetic or recombinant protein domains which specifically recognize sequences in VASP which contain phosphorylated serine 157 and/or threonine 278.

By means of binding to proline-rich peptides, such as zyxin and vinculin, and at the same time binding its own proline-rich amino acid domain to profilin, VASP makes possible the formation of filamentous actin, with the VASP functioning as an adapter molecule. Disturbance of this protein/protein interaction can lead to faulty thrombocyte aggregation or vascular contraction. Thus, the formation of actin/myosin bridges is a prerequisite for the contraction of smooth muscle cells, for example. It has been found that the phosphorylation of VASP at the serine 157 position correlates with inhibition of the fibrinogen receptor glycoprotein IIb/IIIa (Horstrup et al., Eur. J. Biochem., 225, 21–27, 1994). Determination of VASP phosphorylation at the serine 157 position consequently makes it possible to search systematically for substances or drugs which affect the interaction of VASP with its intracellular binding partners and are, for example, suitable for the therapy of cardiovascular diseases which are associated with vascular damage.

Particular preference is also given to the embodiments which are described in the implementation examples.

The following examples serve to clarify the invention and do not restrict it in any way.

EXAMPLES

Example 1

Isolation of a Monoclonal Antibody Against Phosphoserine 239 VASP

A phosphorylated peptide and a non-phosphorylated peptide, each of which encompasses the peptide sequence KLRKVS$^{239}$ KQ or RKVS$^{239}$ KQE around serine 239, are synthesized using an Applied Biosystems peptide synthesizer (Model 431A) in accordance with the Fmoc chemistry which is familiar to the skilled person. The phosphoserine in the phosphorylated peptide is incorporated during peptide synthesis using Fmoc-serine [PO(Obzl)OH—OH] from Cal-biochem. MS-confirmed peptides are purified using RPC and a VYDAC 218TP column (purity>98%).

After having been activated with bromoacetic acid or bromoacetic-N-hydroxysuccinimide ester (Sigma), the peptides which have been prepared in this way are conjugated to thiolated KLH (keyhole limpet hemocyanin, nanoTools). Female Balb/c mice (6 weeks old) are immunized subcutaneously 4×at 14-day intervals with the KLH-phosphopeptide (10 µg/mouse) containing complete Freund's adjuvant in the first injection and incomplete adjuvant in the 3 following injections. The mice are then (2 weeks later) given booster injections of 10 µg of immunogen in PBS (phosphate-buffered saline) on three consecutive days. 1 day after the last booster injection, the mice are sacrificed and the spleens removed. Spleen cells are isolated and fused with non-producing myeloma cells (e.g. PAI-Zellen, J. W. Stockeret al. (1982) Res. Disclosure, 21713) using the established Köhler/Milstein methodology.

A differential screening method using phosphorylated/non-phosphorylated peptide as well as phosphorylated/non-phosphorylated recombinant human VASP is employed to test hybridoma cells for their ability to secrete antibodies against phosphoserine 239 VASP.

For the test using phosphorylated/non-phosphorylated peptide, these peptides are coupled covalently to DNA-BIND-ELISA plates (from Costar) and the hybridoma supernatents are screened using the ELISA method.

Supernatants which recognize phosphopeptide are additionally examined for their ability to recognize completely phosphorylated recombinant (E. coli system) human VASP but not the correspondingly dephosphorylated VASP.

Monoclonal antibodies from the supernatants of the hybridoma cells which have been identified by the above-described methods as being positive can preferably be purified from serum-free hybridoma cell cultures by means of thiophilic adsorption chromatography (POROS 50-OH, nanoTools).

Using different test methods, it was possible to identify and characterize one of the isolated antibodies (clone 16C2) as being a monoclonal antibody of the mouse IgG1κ class which only recognizes VASP when this protein is phosphorylated at the serine 239 position. Antibody 16C2 does not recognize other proteins and other VASP phosphorylation sites under the conditions employed.

Monoclonal antibodies which specifically recognize phosphoserine 157 VASP or phosphothreonine 278 VASP can be isolated in analogy with the above-described method by employing phosphorylated peptides which encompass the known peptide sequences around serine 157 or threonine 278 of the VASP protein, respectively, as the antigen.

The generation of monoclonal antibodies recognizing VASP phosphorylated at Position Ser 239 is also described in Smolenski et al., J.

Biol. Chem., 237, 32, 20029–20035 (1998).

Example 2

Flow-cytometric Analysis of VASP Serine 239 Phosphorylation

Analysis of VASP Serine 239 Phosphorylation in Washed Human Thrombocytes

Human thrombocytes are prepared, and VASP phosphorylation is stimulated by incubating with vasoactive substances, as described (Eigenthaler et al., Eur. J. Biochem., 205, 471–481, 1992). The reaction is stopped by fixing, at room temperature for 10 min, with formaldehyde at a final concentration of approx. 3.5%. After a washing procedure (optional), the cells are permeabilized with Triton X-100 and then washed. Staining is effected by incubating with the appropriate antibody, which is either directly fluorescence-labeled or colored using a second antibody which is fluorescence-labeled. Expediently, 0.5–5 µg, preferably 1–2 µg of primary antibody are employed per ml for this purpose. 1.7 µg/ml are, for example,. suitable when Mab 16C2 is used as the primary antibody. The binding of antibody 16C2 is then determined and analyzed in the flow cytometer as described, for example, in G. Otten and W. M. Yokoyama,(1992) Flow cytometry analysis using the Becton Dickinson FACScan, Current Protocols in Immunology, 5.4.1–5.4.19.

Example 3

Use of Western Blotting to Determine VASP Serine 239 Phosphorylation in Cell Extracts In parallel with the flow cytometry (Example 2), Western blotting is used to determine the phosphorylation of VASP in cell extracts by means of methods which are familiar to the skilled person and which are described, for example, in Eigenthaler et al. (Eur. J. Biochem., 205, 471–481, 1992). The concentration of the antibody employed is expediently between 0.1 and 5, preferably from 0.5 to 1.0, µg/ml, depending on the content of VASP in the sample to be determined. For example, for human thrombocytes and rat thrombocytes it is advantageous to use 0.5 µg of antibody/ ml, while for human umbilical cord endothelial cells it is advantageous to use 1.0 µg of antibody/ml. In principle, analysis of VASP serine 239 phosphorylation in cell extracts by means of Western blot analysis and on fixed cells by means of flow cytometry yielded identical results.

Example 4

Analysis of VASP Serine 239 Phosphorylation in Whole Blood or Platelet-rich Plasma (PRP)

Whole blood or PRP are incubated with vasoactive substances and the incubation is stopped by fixing, at room temperature for 10 min, with formaldehyde at a final concentration of approx. 3.5%. PRP is prepared from whole blood as described in Eigenthaler et al. (Eur. J. Biochem., 205, 471–481, 1992). Thrombocytes in the PRP are pelleted by centrifugation and resuspended in physiological buffer (Eigenthaler et al., 1992, see above). The thrombocytes are permeabilized and then stained as described above for washed thrombocytes.

Example 5

Time Course of the Stimulation of VASP Serine 239 Phosphorylation in Washed Human Thrombocytes Following Treatment with Sodium Nitroprusside (SNP)

Human thrombocytes were treated with 100 µM SNP. Cell samples were withdrawn at times 0, 1, 3 and 5 minutes. The antibody 16C2 wars used to determine the phosphorylation of VASP serine 239 in parallel by means of the Western blot analysis of extracts of the cell samples which had been withdrawn and by means of flow-cytometric determination carried out on the human thrombocytes, which had been fixed and permeabilized as described above. The autoradiograms of the Western blots were analyzed quantitatively using NIH gel-blotting image 1.6 software. The increase in antibody 16C2/phosphoserine 239 VASP binding (% increase (5 min value=maximum effect=100%) is recorded in Table 1.

TABLE 1

| t (min) | % Increase Thrombocytes Cytometry | Cell extract Western blotting |
|---|---|---|
| 0 | 0 | 0 |
| 1 | 62.5 | 83.5 |
| 3 | 89.3 | 95.2 |
| 5 | 100.0 | 100.0 |

Example 6

Use of Antibody 16C2 to Analyze the Phosphorylation of Recombinant VASP by cAMP-dependent Protein Kinase or cGMP-dependent Protein Kinase Purified, recombinant hexahistidine-labeled VASP (25 µg/ml) was phosphorylated by a purified catalytic subunit (11 µg/ml) of cAMP protein kinase (CAPK) or by purified cGMP protein kinase (cGPK; 24 µg/ml). Aliquots were removed from the reaction mixture at the given times, mixed immediately with SDS-containing stop solution, boiled and fractionated by means of SDS-PAGE. Phosphorylation of the VASP was analyzed by Coomassie Blue staining and by Western blotting using either a polyclonal VASP antibody (M4, Halbrügge M. etal. J. Biol. Chem. 265, 3088–3093 (1990), obtainable from:Alexis Corporation, Alte Hauensteinstraße 4, CH-4448 Läufelfingen, Switzerland) or the monoclonal VASP antibody 16C2. The band below VASP in the Coomassie Blue staining is cAPK, while that above VASP is cGMP-PK The SDS-PAGE which was performed demonstrated the change in the migratory behavior of VASP from 46 to 50 kDA due to the phosphorylation of serine 157, which is preferred by 20 cAPK. The phosphorylation of serine 239 (detected by the 16C2 antibody) is preferred by cGMP-PK.

Example 7

Analysis of the Phosphorylation, in Ptk2 Cells, of Transfected VASP Containing Various Phosphorylation Mutations The phosphorylation of transfected human VASP and VASP mutants was investigated in Ptk2 cells. Wild-type VASP and VASP mutants each of which contained mutated (inactivated) phosphorylation sites (alteration of serine 157, serine 238 or threonine 277), were transfected into Ptk2 cells together with human cGMP protein kinase 1β and expressed under the control of the CMV promoter. Ptk2 cells harbor very little endogenous VASP and cGMP protein kinase. Two days after transfection, the cells were incubated for 30 min with 30 µM 8pCPT-cGMP and cell extracts were then isolated. The phosphorylation of VASP in these cell extracts was then investigated in Western blots using the polyclonal antibody M4 and the monoclonal antibody 16C2. A phosphorylation-dependent change of VASP from 46 kDa to 50 kDa was no longer present when serine 157 was inactivated (mutation S157A). A signal recognized by antibody 16C2 was no longer present when serine 239 was inactivated (S239A). In these analyses, mutations of threonine 277 behaved like wild-type VASP.

Example 8

Analysis of the Phosphorylation of VASP in Human Thrombocytes Following Stimulation with Various Vasodilators and cAMP/cGMP Analogs Washed human thrombocytes ($0.7 \times 10^9$ cell/ml) were incubated with 1 μM Pg-$I_2$ (prostacyclin), 0.5 mM 5,6-DCI-cBIMPS (cell membrane-permeable cAMP analog), 10 μM SNP (sodium nitroprusside) or 1 mM 8pCPTcGMP (cell membrane-permeable cGMP analog). Aliquots ($2.8 \times 10^7$ cells) were removed after the given times, mixed with the SDS stop solution and boiled, and then investigated for VASP phosphorylation using the Western blotting method. The analyses were carried out using the polyclonal antibody M4 or the monoclonal antibodies 16C2. Serine 157 phosphorylation was quantified by the shift of VASP from 46 to 50 kDa, while serine 239 phosphorylation was quantified by means of the signal given by the 16C2 antibody.

Example 9

Phosphorylation of VASP in rat Thrombocytes

Rat thrombocytes ($0.7 \times 10^9$ cell/ml) were incubated for 5 min with 100 μM sodium nitroprusside (SNP), with 10 μM prostaglandin E1(PgE1) or without either of these additions. The extracts of these rat thrombocytes were analyzed by Western blotting. The blot demonstrated that the 5 phosphorylation-dependent shift of VASP from 46 kDa to 50 kDa (serine 157 phosphorylation) and the phosphorylation-dependent signal given by the 16C2 antibody (serine 239 phosphorylation) also took place in rat thrombocytes. Similar results are also obtained using mouse thrombocytes.

Example 10

Immunofluorescence Investigations of VASP and Phospho-VASP Carried out on Human Thrombocytes Human thrombocytes (in platelet-rich plasma, PRP) were deposited on a glass slide and were allowed to attach and spread for 45 min. These thrombocytes were then incubated on the glass slide for 15 min without (A and C) or with 100 μM 8pCPTcGMP (B and D). The cells were then immediately fixed with 4% paraformaldehyde and permeabilized with 0.2% Triton X-100. They were then incubated with the polyclonal antibody M4 (1:1000) or the monoclonal antibody 16C2, followed by the usual secondary antibodies. Photographs show the appearance of the phosphorylation-dependent signal when the 16C2 antibody is used, whereas the signal with the polyclonal M4 antibody (in the immunofluorescence, the sum of 46 kDa and 50 kDa VASP since there is no fractionation) is phosphorylation-independent.

What is claimed is:

1. An antigen binding protein which only binds VASP (vasodilator-stimulated phosphoprotein) as antigen when VASP is present in phosphorylated form, wherein said VASP is in the natural form or is a functionally equivalent moiety, mutant, fragment or variant thereof and wherein the antigen binding protein is monoclonal antibody 16C2 which is produced by the hybridoma cell line 16C2 deposited at the Deutsche Sammiung von Mikroorganismen und Zellkulturen under the No. DSM ACC2330.

2. The hybridoma cell line 16C2 (DSM ACC2330), which produces the monoclonal antibody of claim 1.

3. A diagnostic kit, comprising an antigen binding protein which only recognizes VASP as antigen when VASP is present in phosphorylated form, wherein said VASP is in the natural form or is a functionally equivalent moiety, mutant, fragment or variant thereof and wherein the antigen binding protein is monoclonal antibody 16C2 which is produced by the hybridoma cell line 16C2 deposited at the Deutsche Sammiung von Mikroorganismen und Zeilkulturen under the No. DSM ACC2330.

* * * * *

UNITED STATES PATENT AND TRADEMARK OFFICE
CERTIFICATE OF CORRECTION

PATENT NO. : 6,649,421 B1
DATED : November 18, 2003
INVENTOR(S) : Martin Eigenthaler et al.

It is certified that error appears in the above-identified patent and that said Letters Patent is hereby corrected as shown below:

<u>Title page</u>,
Item [54], Title, "PHOSHORYLATED" should read -- PHOSPHORYLATED --.

<u>Column 14</u>,
Line 29, "Sammiung" should read -- Sammlung --.
Line 41, "Sammiung von Mikroorganismen und Zeilkulturen" should read
-- Sammlung von Mikroorganismen und Zellkulturen --.

Signed and Sealed this

Sixth Day of April, 2004

JON W. DUDAS
*Acting Director of the United States Patent and Trademark Office*